United States Patent [19]

Han

[11] Patent Number: 6,125,193
[45] Date of Patent: Sep. 26, 2000

[54] METHOD AND SYSTEM FOR HIGH ABSORPTION OBJECT ARTIFACTS REDUCTION AND SUPERPOSITION

[75] Inventor: Kyung S. Han, Arlington Heights, Ill.

[73] Assignee: Kabushiki Kaisha Toshiba, Kawasaki, Japan

[21] Appl. No.: 09/087,970

[22] Filed: Jun. 1, 1998

[51] Int. Cl.$^7$ ...................................................... G06K 9/00
[52] U.S. Cl. ............................................ 382/131; 382/275
[58] Field of Search .................................... 382/128, 131, 382/132, 199, 270, 275; 378/7, 62, 86, 87, 98.4

[56] References Cited

U.S. PATENT DOCUMENTS

| | | | |
|---|---|---|---|
| 4,590,558 | 5/1986 | Glover et al. | 364/414 |
| 5,243,664 | 9/1993 | Tuy | 382/6 |
| 5,615,279 | 3/1997 | Yoshioka et al. | 382/131 |
| 5,878,102 | 3/1999 | Kalvin | 378/8 |
| 5,953,444 | 9/1999 | Joseph et al. | 382/131 |

OTHER PUBLICATIONS

Willi A. Kalender, Ph.D. et al."Reduction of CT Artifacts Caused by Metallic Implants" *Radiology*, vol. 164, No. 2, pp. 576–577, Aug. 1987.

D. Felsenberg et al."Reduction of Metal Artifacts in Computed Tomography—Clinical Experience and Results" Radiology, Nuclear Medicine and Physical Therapy Clinic, Department of Diagnostic Radiology, 8 pages, (No Date).

Gary H. Glover et al. "An Algorithm for the Reduction of Metal Clip Artifacts in CT Reconstructions" General Electric Company, Medical Systems Division, Applied Science Laboratory, pp. 799–807, *Med. Phys* 8(6), Nov./Dec. 1981.

Ge Wang et al. "Interative Deblurring for CT Metal Artifact Reduction" *IEEE Transactions on Medical Imaging*, vol. 15., No. 5, Oct. 1996, pp. 657–664.

Alan D. Kalvin et al. "Using Scout Images to Reduce Metal Artifacts in CT with Application to Revision Total Hip Surgery" 12 pages, (No Date).

Heang K. Tuy, "A Post–Processing Algorithm to Reduce Metallic Clip Artifacts in CT Images" *Eur. Radiol.* 3, 129–134 (1993).

Heang K. Tuy, "An Algorithm to Reduce Clip Artifacts in CT Images", SPIE vol. 1652, Medical Imaging CI: Image Processing (1992) pp. 635–643.

"Computerized Tomographic Imaging", "Algorithms for Reconstruction with Nondiffracting Sources", pp. 56–59 (No Date).

Kyung Han, et al. "Metal Pin Artifacts Reduction and Superposition", International Technical Exhibition of Medical Imaging 1998, 57th Japan Radiological Society, 54th Japanese Society of Radiological Technology, Kobe, Japan, Apr. 9–11, 1998.

*Primary Examiner*—Andrew W. Johns
*Attorney, Agent, or Firm*—Oblon, Spivak, McClelland, Maier & Neustadt, P.C.

[57] ABSTRACT

Method and system for the reduction of artifacts from high absorption objects, such as metal pins. From an image, such as a computed tomography image, an image of the high absorption object is extracted by thresholding. A boundary of the object in the image is estimated. This information is used to modify the projection data to reduce the artifacts due to the object. The projection data may be rebinned from fan beam to parallel beam. After the projection data is modified the parallel beam projection data is reconstructed and the high absorption object image previously extracted may be superimposed on the reconstructed image. The original, modified and superimposed images may be displayed and compared.

47 Claims, 7 Drawing Sheets

METHOD AND SYSTEM FOR HIGH ABSORPTION OBJECT ARTIFACTS REDUCTION AND SUPERPOSITION

BACKGROUND OF THE INVENTION

1. Field of the Invention

The present invention is related to the correction of artifacts in image processing and, more specifically, to the reduction of high absorption object artifacts in computed tomography.

2. Discussion of Background

There have been many different approaches to minimizing artifacts from high absorption objects, such as metal pins, in medical images. H. K. Tuy in *An Algorithm to Reduce Clip Artifacts in CT Images*, SPIE vol. 1652 Med. Imaging VI: Image Processing pp. 635–43 (1992), and in *A post-processing algorithm to reduce metal clip artifacts in CT images*, Eur. Radio. 3, 129–134 (1993) describes a two-phase algorithm where first a crude compensation for beam hardening is performed followed by a refinement phase. Kalender et al, *Reduction of CT Artifacts Caused by Metallic Implants*, Radiology, vol. 164, no. 2, pp. 576–7 (1987) describes an artifact reduction routine where the metallic implant is delineated by an operator on the image using a light pen. Approaches also include image processing, iterative reconstruction, beam hardening correction and partial volume correction. While the last two correction techniques of the above-mentioned methods have been used to improve image quality, prior methods have not been effective in handling metal pin artifacts, especially severe metal pin artifacts such as star pattern artifacts, streak artifacts and blooming artifacts, nor have they been effective in recovering diagnostic information obscured by these artifacts.

SUMMARY OF THE INVENTION

An object of the invention is to remove high absorption object artifacts from images.

Another object of the invention is to remove high absorption object artifacts from an image while superimposing data corresponding to the object onto the image.

It is a further object of the invention to eliminate or minimize star pattern artifacts in images.

A still further object of the invention is to recover obscured information while achieving the above objects.

Still another object is to remove metal pin artifacts automatically.

Yet another object of the invention is to remove artifacts and recover obscured information in a rapid manner.

These and other objects of the invention are achieved by a method and system using image processing to eliminate or minimize high absorption object artifacts in images. The image processing method according to the invention can include obtaining an image of a subject and extracting a high absorption object image from this image. Boundary information of the high absorption object is generated and projection data is modified using the boundary information. The method may also include a step of superimposing high absorption object data on the modified image. The method can advantageously display each or all of the image, an image with the high absorption object image removed and an image having superimposed high absorption object data.

The high absorption object image may be extracted from the image by thresholding. Also, generating the boundary information may incorporate a central slice theorem and connectivity checking may be incorporated to verify and correct multiple high absorption objects. Connectivity checking may consist of looking at the number of channel that separate two objects. For example, if the objects are within a certain number of channels, the objects will be combined.

The method also can generate projection data corresponding to the image and modifying the projection data using the boundary information. The projection data may be modified by smoothing portions corresponding to the high absorption object image which have been extracted from the data. The smoothing may be accomplished by evaluating pixels surrounding the areas of high absorption object extraction. The image, or features in the image, may also be taken into consideration in modifying the projection data. It is also advantageous to rebin the projection data before its modification.

The method may also include a step of reconstructing the image using the modified projection data, or the modified rebinned projection data. The metal pin data is preferably superimposed on the reconstructed image.

These and other objects are also achieved by an image processing system having a high absorption object extraction circuit, a high absorption object boundary estimation circuit connected to the extraction circuit, a projection data modification circuit connected to the estimation circuit and an image reconstruction circuit connected to the modification circuit. The system may also include a projection data memory circuit and a rebinning circuit connected to the memory circuit and the modification circuit.

The extraction circuit may extract a high absorption object image from the image. The modification circuit may modify areas of the image corresponding to the extracted high absorption object image and the reconstruction circuit may reconstruct the image using a modified image produced by the projection data modification circuit and boundary information from the estimation circuit. The reconstruction circuit preferably uses rebinned projection data produced by a rebinning circuit connected to the modification circuit.

The estimation circuit may generate boundary information of the high absorption object. A superposition circuit connected to the reconstruction circuit may superimpose high absorption object data on the image. The estimation circuit may also use a central slice theorem or connectivity checking to estimate the boundary of the high absorption object.

The system may also include a Fourier analysis circuit connected to the extraction and estimation circuits. The Fourier analysis circuit may perform a Fourier transform on the image to produce another image, or image data, which is or are used by the estimation circuit to estimate the high absorption object boundary.

BRIEF DESCRIPTION OF THE DRAWINGS

A more complete appreciation of the invention and many of the attendant advantages thereof will be readily obtained as the same becomes better understood by reference to the following detailed description when considered in conjunction with the accompanying drawings, wherein:

FIGS. 6A–6C are images of two stainless surgical pins in a water phantom, where FIG. 6A is an original image, FIG. 6B is an image with modified projection data and FIG. 6C is the metal pin superimposed image; and FIGS. 7A–7C are images of a clinical hip joint, where FIG. 7A is an original image, FIG. 7B is the image with modified projection data and FIG. 7C is the metal pin superimposed image.

DESCRIPTION OF THE PREFERRED EMBODIMENT

Figure 1:
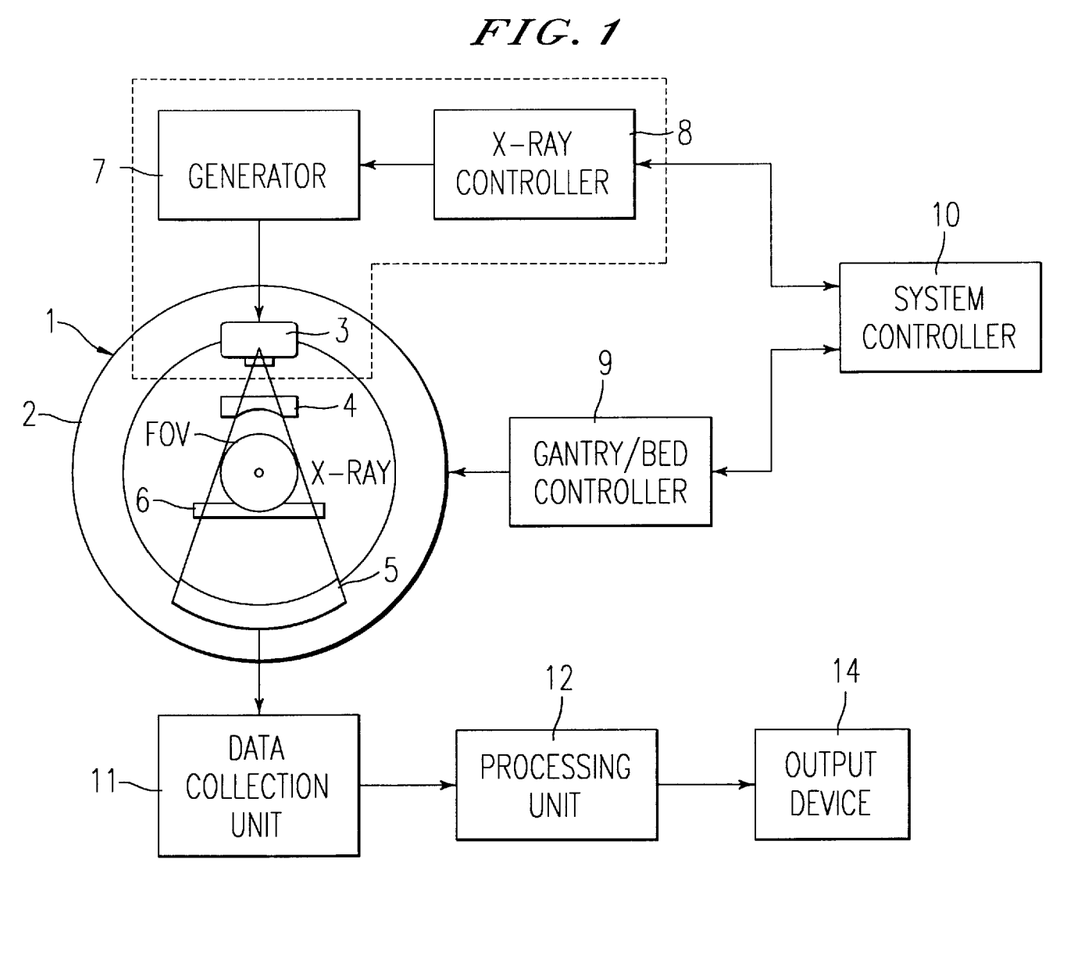
FIG. 1 is a diagram of the system according to the invention.

Referring now to the drawings, wherein like reference numerals designate identical or corresponding parts throughout the several views, and more particularly to FIG. 1 which is a diagram of the system according to the invention. A gantry 1 accommodates an x-ray source 3 that generates a beam of x-rays. An x-ray detector 5 receives the x-rays emitted from source 3 after penetrating the subject indicated as field of view (FOV). X-ray source 3 and detector 5 are installed on a rotating ring 2. The system may also include an x-ray filter 4 which may be coupled to rotating ring 2. The subject is typically laid on a sliding sheet of a bed 6.

X-ray controller 8 supplies a trigger signal to high voltage generator 7. High voltage generator 7 applies a high voltage to x-ray source 3 based upon the received trigger signal. X-rays are emitted by x-ray source 3 and gantry/bed controller 9 synchronously controls the revolution of rotating ring 2 of gantry 1 and the sliding of the sliding sheet of bed 6 to scan the subject. System controller 10 constitutes a control center of the entire system and controls the x-ray controller 8 and gantry/bed controller 9 such that, as seen from the subject, x-ray source 3 executes scanning, preferably along a helical path. However, the invention is not limited to helical scanning and other scanning techniques may be used.

The output signal of the detector 5 is amplified by data collection unit 11 and converted into a digital signal to produce projection data. Data collection unit 11 also outputs projection data 15 to processing unit 12. Processing unit 12 processes the data using the techniques described above to produce output images. The particular image required, such as the original image, the threshold image or the superimposed image may be output to output device 14. Output device 14 may consist of a video display terminal, a laser printer, another output device, or a combination of these.

Figure 2:
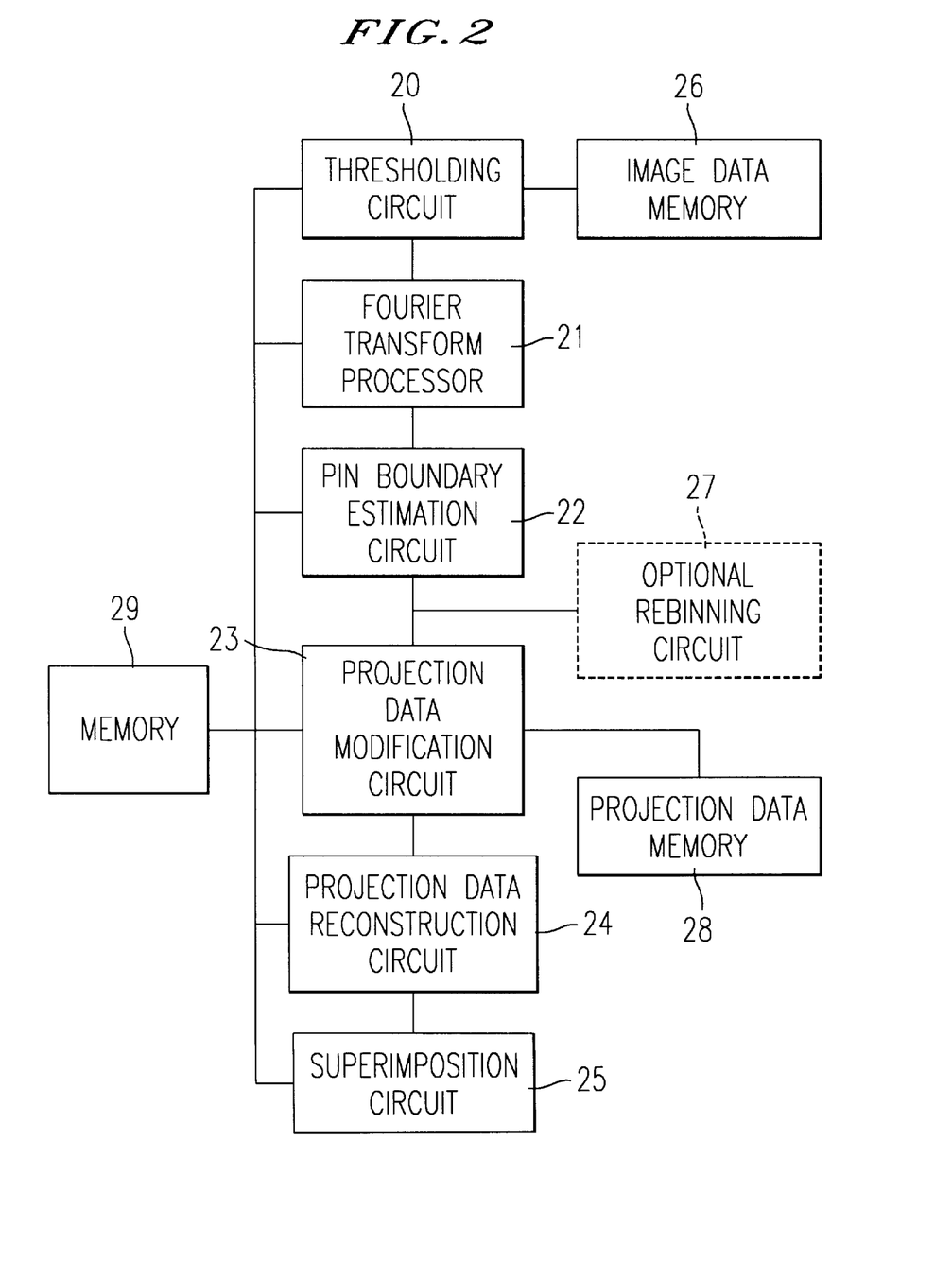
FIG. 2 is a diagram of an image processor according to the invention.

A more detailed view of the extraction and superposition circuitry in processing unit 12 according to the invention is shown in FIG. 2. The circuit of FIG. 2 includes a thresholding circuit 20. Circuit 20 thresholds the image data received from image data memory 26 to remove the high absorption object image. In this embodiment a metal pin was selected to illustrate the invention. However, the invention is not limited to metal pins but is applicable to other high absorption objects such as surgical clips. The threshold is a preselected value or may be automatically selected by the system based upon the image. The threshold may be selected using such criteria as the type of image and the features in the image, or by histogram analysis. The metal pin image data is extracted and stored in memory 29. CT values for the artifacts are much lower than those of metal pins.

The image after extracting the metal pin image is sent to Fourier transform processor 21 which conducts a two-dimensional fast Fourier transform. Typically, the image is of 512×512 size and the image after processing by circuit 21 is a 1024×1024 image in the frequency domain. The image produced by circuit 21 is then sent to pin boundary estimation circuit 22. A pin boundary estimation routine is carried out on the image output by circuit 21 to estimate the metal pin boundaries.

Using the information from the circuit 22, the projection data modification circuit 23 modifies the projection data from circuit 28. The projection data is smoothed in the areas where the metal pin image was extracted. The smoothing is performed based upon the pixel values surrounding the extracted areas. Other factors such as the type of image or the type of features in the image may be taken into consideration in smoothing the projection data. An optional rebinning circuit 27 can be included where the projection data from memory 28 is rebinned from parallel beam data to fan beam data.

Circuit 23 receives other information from, for example, memory 29 regarding the threshold value used for the boundary information, the number of the projection, the number of channels for smoothness, the FOV of the input image and the threshold value for the connectivity checking. The connectivity checking is done to determine whether the metal pins are close to one another. They will be combined if the pins are within a certain distance, such as within a range of 3–7 channels. Other distances may be appropriate in other cases.

The connectivity checking acts to further minimize the metal pin artifacts since multiple pins may interfere with the correction process. If more than one metal pin is present in an image, metal pin artifacts may not be effectively minimized when they are located close to each other or are clustered together. If the locations of the metal pins are determined, replacing the metal pin information with the surrounding background information will lose its effectiveness in reducing metal pin artifacts. Some background information may be metal pin information itself and generate different types of artifacts.

The projection data is then reconstructed after modification with the same scaling as the original image by projection data reconstruction circuit 24. Superimposition circuit 25 can superimpose an image of the metal pin onto the reconstructed image. The original pin image is superimposed on the artifact-reduced image. Superimposition circuit 25 can receive the extraction information from, for example, memory 29 which stores information from thresholding circuit 20, the pin boundary estimation circuit 22 and projection data modification circuit 23.

Either the original image, the image with the artifacts removed or the superimposed image can be sent to the output device 14 for display or hard copy.

It should be noted that memory 29 may also include areas to store values used during the calculations by the various circuits 20–25, and that memories 26, 27 and 29 could be implemented as a single memory with different areas allocated to the different types of data stored in the memories 26, 27 and 29 described above.

The system according to the invention may also be implemented in software using a programmed computer. In this case, the operations of the system controller 10 and processing unit 12 may be carried out using a single computer or separate computers. The invention may also be implemented as a computer readable storage medium, such as a floppy disk or a optical disk.

Figure 3:
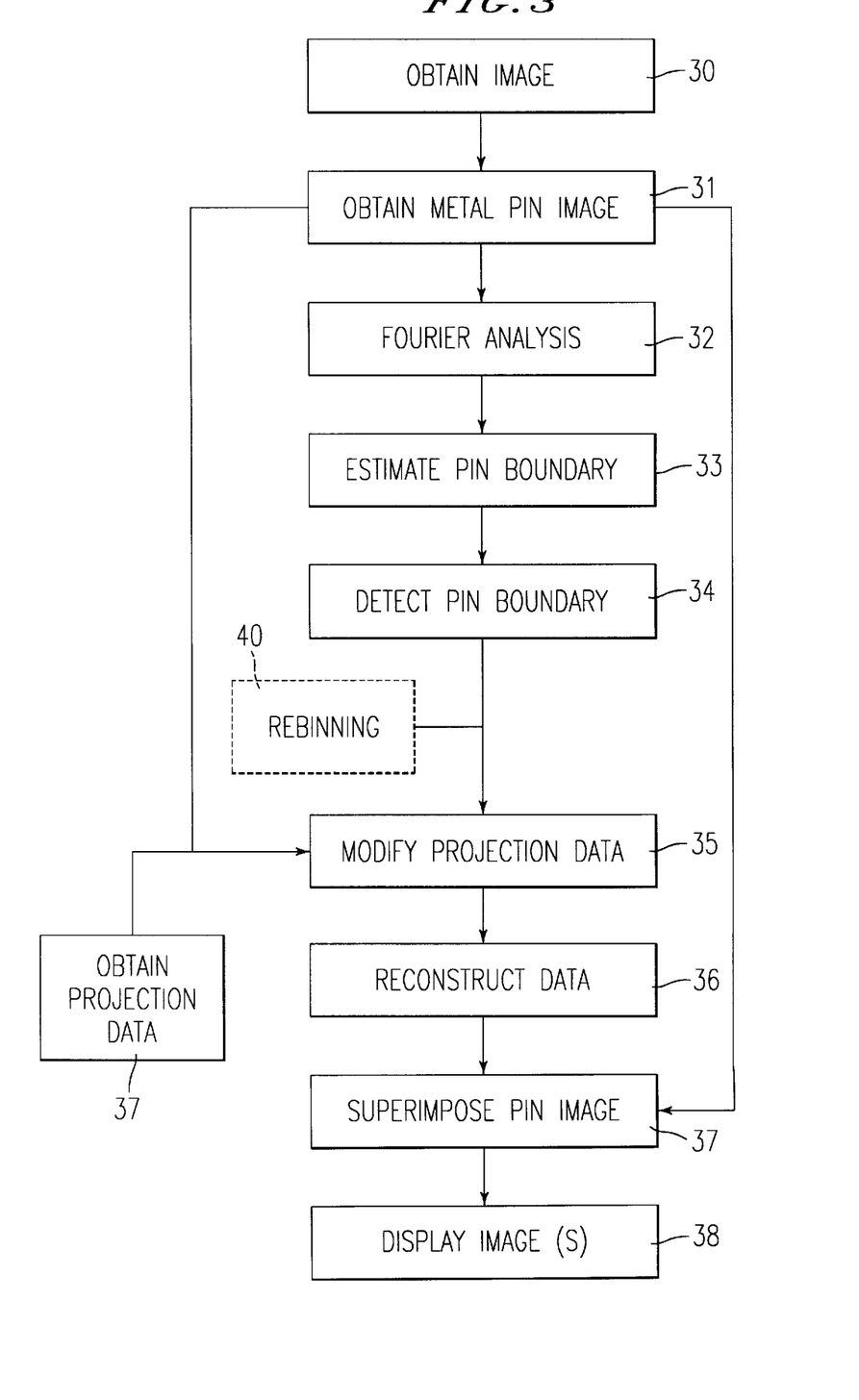
FIG. 3 is a flow chart of the method according to the invention.

FIG. 3 is a flow chart of the method according to the invention. The following also describes in more detail the functions carried out by the system according to the invention. In step 30 an image is obtained. In this example the image is a computed tomography (CT) image, but other images may be used. The image is obtained by irradiating a subject with x-rays and detecting the x-rays after they have passed through the subject. From the detected x-rays a digital gray-level image is generated typically of 512×512 pixels, but other sizes may be used.

Next, a metal pin image is extracted from the original image by gray-level thresholding in step 31. This thresholding is accomplished in a straight-forward manner since the CT values of artifacts and background (i.e., patient tissue) are much lower than those of high absorption objects, such as metal pins. The method automatically extracts the image of the object based upon a threshold previously selected. The locations and gray-level value of the pixels corresponding to the object are stored in memory for later use. The selection of the threshold is made empirically, based upon experimentation. The image of the object has a brighter appearance than many of the pertinent features in the image and can be extracted from the image without diminishing or removing these features in the image. The threshold value may be may be selected based upon the type of image used, the type of object, the type of anatomical features in the image or other considerations, and may be typically in a range of 700–1200. In this example a threshold of 1000 was chosen.

In this example, a metal pin image is extracted. From the metal pin image, which is typically a 512×512 image, a 1024×1024 image is produced by Fourier analysis. One can estimate the metal pin boundary information on a pixel-by-pixel basis, but Fourier analysis is the most accurate and fastest way to estimate the metal pin boundary information from the metal pin images. This is typically done taking a two-dimensional fast Fourier transform (2D FFT) in the frequency domain (step 32). This image is produced for the estimation of the metal pin boundaries in the next step of the procedure, the central slice theorem.

Figure 4:
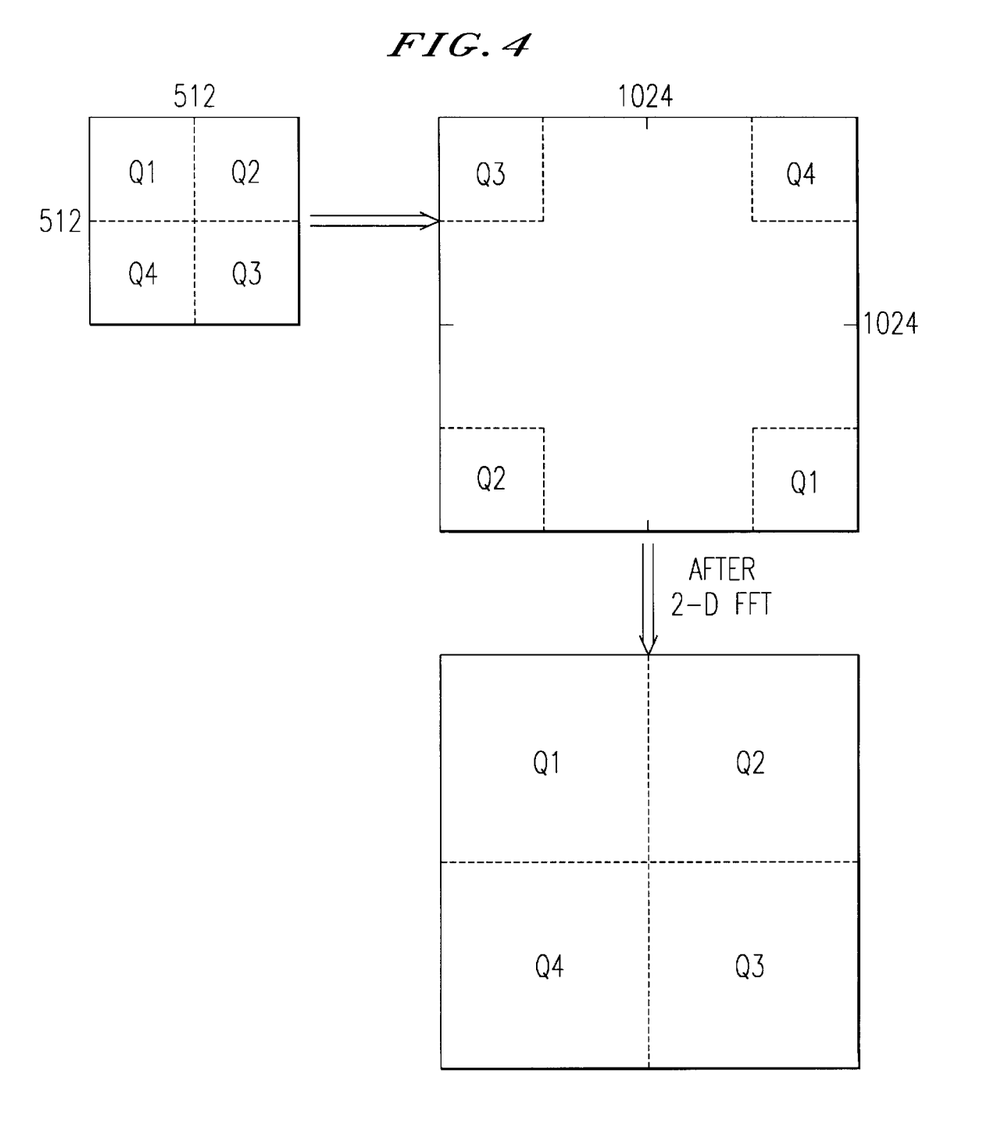
FIG. 4 is a diagram illustrated 2-D Fourier transformation processing.

The metal pin image (512×512) is transformed into 1024×1024 real and imaginary images in the frequency domain by 2-D FFT processing. This process is illustrated in FIG. 4. These 1024×1024 real and imaginary images will be utilized to estimate the metal pin boundary information through the Central Slice Theorem for any number of views, some thresholding and differentiation will be applied to locate the metal pin boundaries. The central slice theorem is described, for example, in Kak et al, *Principles of CT Imaging*, IEEE Press, New York (1989) at pp. 56–59, which is herein incorporated by reference.

The pin boundaries are estimated in step 33. The central slice theorem is the preferred method to produce metal pin boundary information for either 180° or 360° rotation.

From the metal pin boundary information produced using the central slice theorem and the projection data the boundaries of the metal pins can be automatically detected (step 34). The projection data, which is typically collected in fan beam form (step 39), can be rebinned to parallel beam data (step 40). The projection data is modified in step 35 based upon the boundary information to reduce the artifacts due to the metal pins. After application of the central slice theorem, the projection data space representation of the pin is generated. Thus, the original projection data can be modified to remove the pin information in the common data elements.

The projection data is smoothed in the areas of the image extracted in the metal pin extraction process. The smoothing may be done based upon values of pixels surrounding the extracted areas. The type of image and the type of features in the image may be also be taken into consideration in the smoothing. This routine uses information such as the threshold value for the boundary information, the number of the projection, the number of channels for smoothness, the field of view (FOV) of the input image and the threshold value for connectivity checking. These parameters may be varied based upon the image used, etc., to minimize the effect of the metal pin artifacts. For example, the connectivity checking is used to determine whether the metal pins are close to each other. If the pins are within a given distance, the pins will be combined.

The metal pin boundary information on the original image can be estimated on a pixel by pixel basis for each channel and view. The boundary information can be utilized to modify the fanbeam projection data, but the process can be very time consuming and some approximations are involved in the estimation. With the use of the central slice theorem the boundary information can be estimated easily and accurately from the 1024×1024 real and imaginary frequency domain images.

Figure 5:
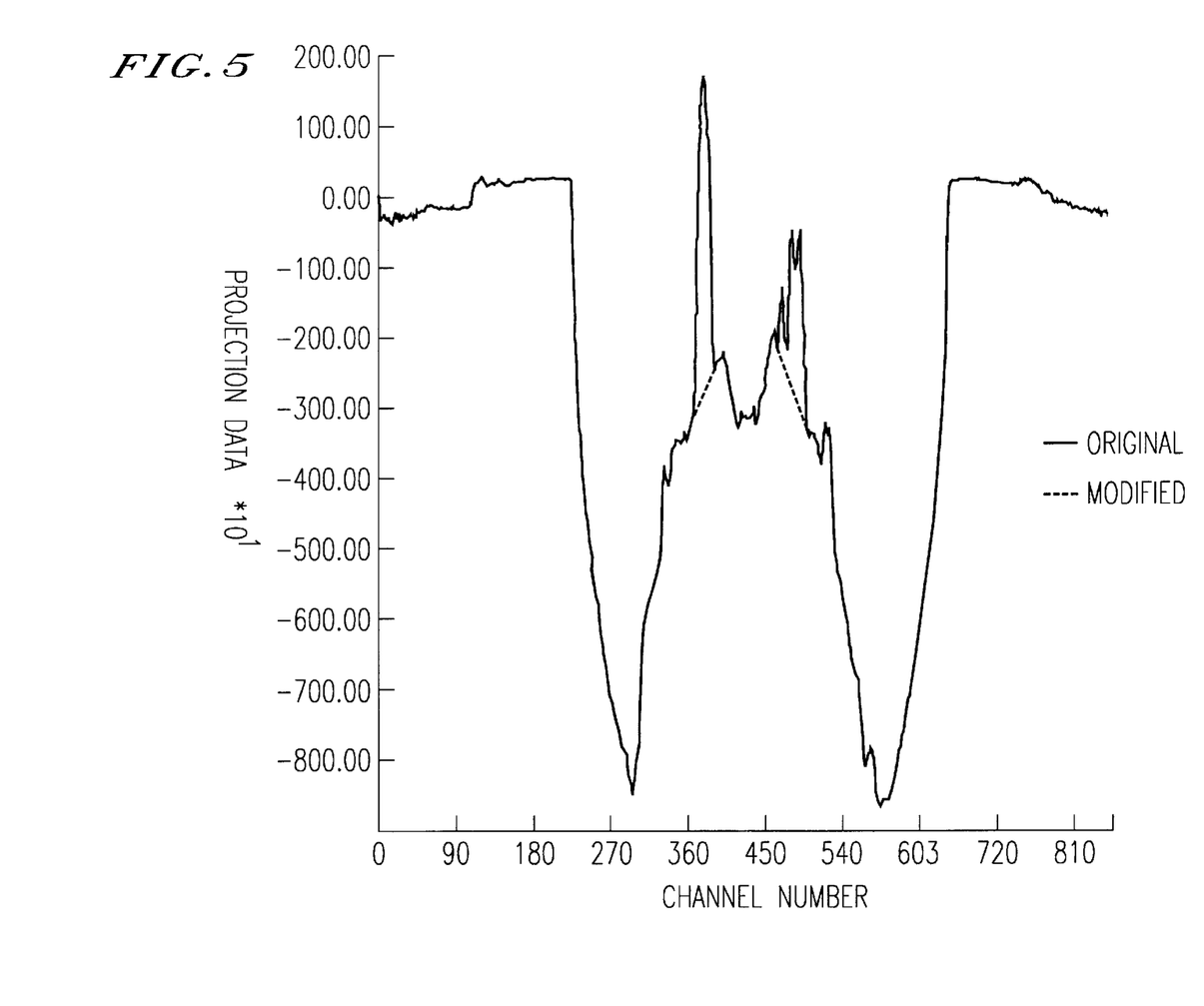
FIG. 5 is a graph illustrating original and modified projection data.

FIG. 5 is a graph of original and modified projection data. The data having the high CT values corresponds to the pins and can be eliminated. The data extracted corresponding to the pins may be replaced by smoothing the data based upon adjacent pixel values, as discussed above. Other techniques, such as linear approximation or curve-fitting, may be used. The boundary information is again used to extract data, and replacement data is again generated.

After the projection data is modified, the modified fanbeam beam projection data will be reconstructed with the same gray-level scaling (e.g., Hounsfield units) and display matrix as the original image, i.e., 512×512 pixels (step 36). The original image was generated with the fanbeam projection data and a system scaling constant. The same scaling constant is used to generate metal pin artifacts reduced image with the modified fanbeam projection data.

In step 37 the metal pin image extracted from the original image in step 31 is superimposed on the newly constructed modified image. Thus, up to three images can be displayed (original, modified and superimposed images) under the identical condition to see the differences among them (step 38). The images do not have to be displayed but may be stored for later use, or printed.

Figure 6A:
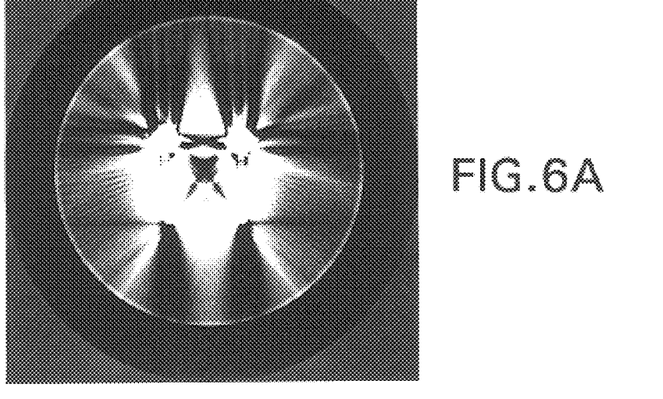
Figure 6B:
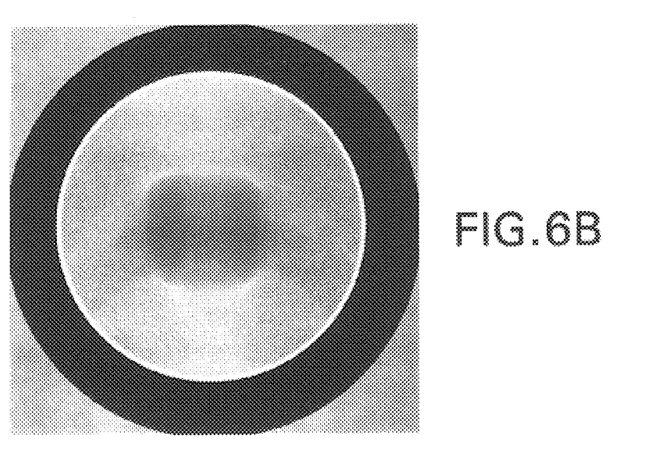
Figure 6C:
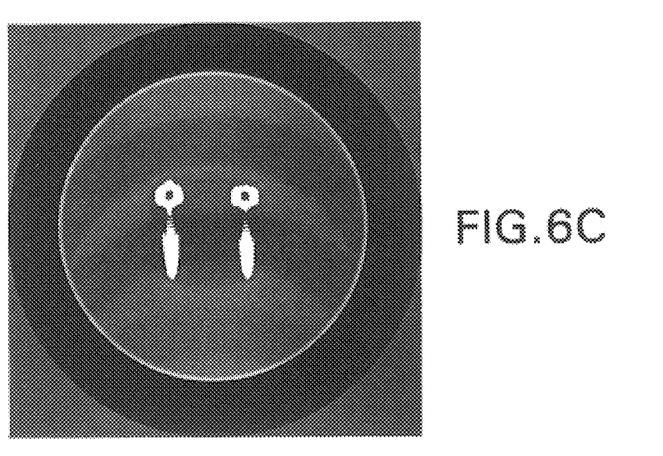

An example of the method is shown in FIGS. 6A–6C. FIG. 6A is the original image of a water phantom having two stainless steel surgical pins. FIG. 6B is the image resulting from the modified projection data, and FIG. 6C is the image with the metal pin extracted in the boundary detection step superimposed on the image of FIG. 6B. In FIG. 6C the artifacts associated with the metal pins are greatly reduced.

Figure 7A:
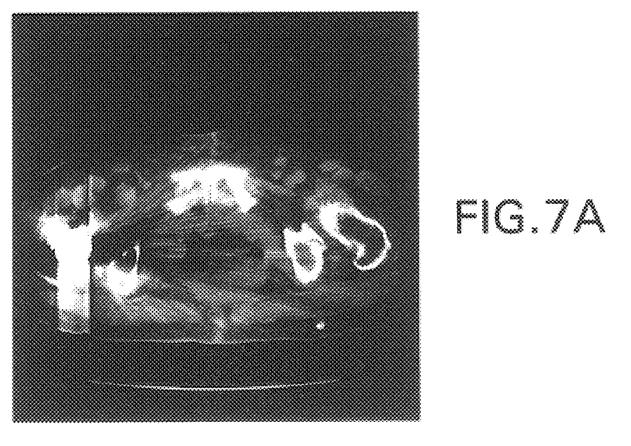
Figure 7B:
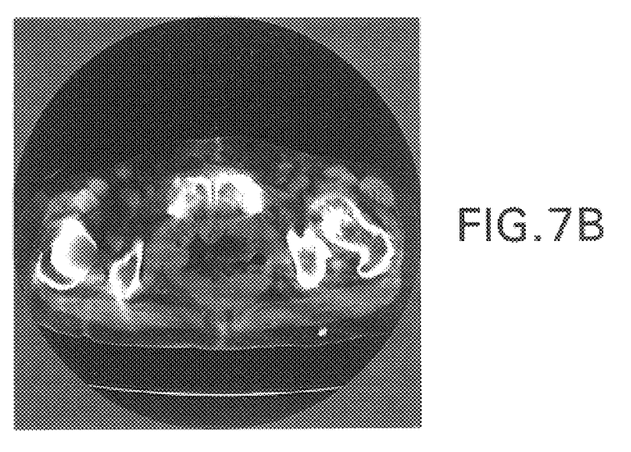
Figure 7C:
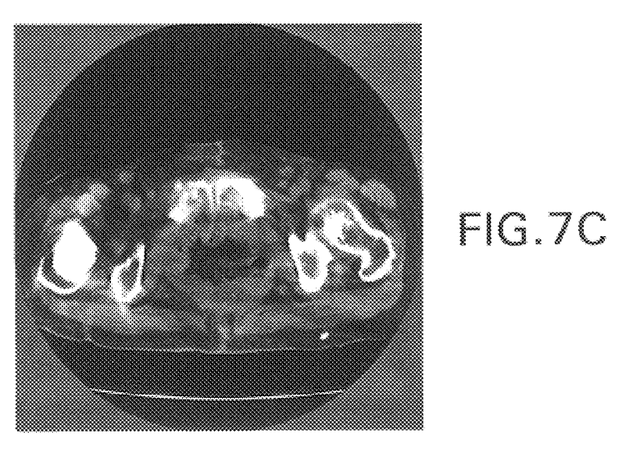

Another example of the method according to the invention is shown in FIGS. 7A–7C. Similar to FIGS. 6A–6C, FIG. 7A represents the original image data of a clinical hip joint having a pin on the left-side hip joint. FIG. 7B is the modified projection data image resulting from the processing through step 36. Finally, FIG. 7C is the modified projection data image having the metal pin extracted in the boundary detection and modification step superimposed. Again, it is clear that the artifacts resulting from the metal pin are greatly reduced, and obscured information due to metal pin artifacts is recovered.

The method and circuit according to the invention may be further improved by refining the connectivity checking method and function, respectively. In the above example, connectivity checking was carried out by looking at the number of channels that separate the objects. It is also possible to interactively analyze the separation between objects. Two objects may have different separations in different views. In some views the objects may be clearly separated while in others they may be very close or even overlap. The connectivity checking of the objects may be performed on a view-by-view basis to improve the removal and recovery processes.

The present invention has the advantage of removing artifacts and recovering obscured information rapidly. This is due in part to the fact that the method and system according to the invention can work with the projection data. The speed of the method and system also benefits from the connectivity checking of the objects.

Further, it is obvious that numerous other modifications and variations of the present invention are possible in light of the above teachings. For example, the invention may be applied to images other than CT images and the invention may be applied to high absorption object artifacts other than the example of hip joint pins used to illustrate the invention such as artifacts arising from dental implants, the neck, or extreme images. It is therefore to be understood that within the scope of the appended claims, the invention may be practiced otherwise than as specifically described herein.

What is claimed as new and desired to be secured by Letters Patent of the United States is:

1. An image processing method, comprising:
  obtaining a radiographic image of a subject;
  extracting a high absorption object image from said radiographic image;
  generating boundary information of said high absorption object; and
  modifying said radiographic image using said boundary information.

2. A method as recited in claim 1, comprising:
  producing a modified image using said modifying step; and
  superimposing high absorption object data on said modified image.

3. A method as recited in claim 1, wherein said extracting step comprises:
  thresholding said radiographic image.

4. A method as recited in claim 1, wherein said generating step comprises:
  estimating a boundary of said high absorption object; and
  detecting said boundary of said high absorption object.

5. A method as recited in claim 4, wherein said estimating step comprises:
  using a central slice theorem.

6. A method as recited in claim 4, wherein detecting said boundary comprises:
  performing connectivity checking.

7. A method as recited in claim 6, wherein performing connectivity checking comprises:
  determining a distance between at least two high absorption objects.

8. A method as recited in claim 6, wherein performing connectivity checking comprises:
  performing connectivity checking using at least two views of said radiographic image.

9. A method as recited in claim 4, comprising:
  generating projection data; and
  modifying said projection data using said boundary.

10. A method as recited in claim 9, comprising:
  using at least one of a threshold value, a projection number, a number of channels, and a field-of-view of said subject in said step of modifying said projection data.

11. A method as recited in claim 9, wherein said step of modifying said projection data comprises:
  performing connectivity checking.

12. A method as recited in claim 9, comprising:
  reconstructing said radiographic image using said modified projection data.

13. A method as recited in claim 12, comprising:
  superposing a high absorption object image on a reconstructed image.

14. A method as recited in claim 9, comprising:
  rebinning said projection data; and
  modifying rebinned projection data.

15. A method as recited in claim 14, comprising:
  reconstructing said radiographic image using said modified rebinned projection data.

16. A method as recited in claim 15, comprising:
  superposing a high absorption object image on a reconstructed image.

17. A method as recited in claim 1, comprising:
  generating projection data corresponding to said radiographic image;
  performing Fourier analysis on said image after extracting said high absorption object image to produce a second image;
  estimating a boundary of said high absorption object using said second image;
  using information generated in said estimating step to detect a boundary of said high absorption object;
  modifying said projection data using said boundary; and
  reconstructing said radiographic image using modified projection data.

18. A method as recited in claim 17, comprising:
  superposing a high absorption object image on a reconstructed image.

19. A method as recited in claim 17, wherein said estimating step comprises using a central slice theorem.

20. A method as recited in claim 1, comprising:
  generating parallel beam projection data associated with said radiographic image;
  modifying said parallel beam projection data using said boundary information; and
  reconstructing said radiographic image using modified parallel beam projection data.

21. A method as recited in claim 1, wherein said extracting step comprises:
  removing said high absorption object image and high absorption object artifacts from said radiographic image.

22. A method as recited in claim 21, comprising:
  generating parallel beam projection data associated with said radiographic image;
  removing said high absorption object image and high absorption object artifacts from said parallel beam projection data;
  modifying said parallel beam projection data using said boundary information; and
  reconstructing said radiographic image using modified parallel beam projection data.

23. A method as recited in claim 22, wherein said modifying step comprises smoothing said projection data in areas corresponding to said high absorption object image and said high absorption object artifacts.

24. A method as recited in claim 1, wherein said modifying step comprises smoothing said radiographic image in areas corresponding to said high absorption object image and high absorption object artifacts.

25. A method as recited in claim 1, wherein said high absorption object is a metal pin.

26. An image processing system, comprising:
   a high absorption object extraction circuit connected to receive a radiographic image;
   a high absorption object boundary estimation circuit connected to said extraction circuit;
   an image modification circuit connected to said estimation circuit; and
   an image reconstruction circuit connected to said modification circuit.

27. A system as recited in claim 26, comprising:
   a projection data memory circuit; and
   a rebinning circuit connected to said memory circuit and said modification circuit.

28. A system as recited in claim 26, wherein said extraction circuit comprises a thresholding circuit.

29. A system as recited in claim 26, comprising:
   said extraction circuit extracting a high absorption object image from said radiographic image;
   said image modification circuit modifying areas of said radiographic image corresponding to said high absorption object image; and
   said reconstruction circuit reconstructing said radiographic image using a modified image produced by said image modification circuit and boundary information from said estimation circuit.

30. A system as recited in claim 26, comprising:
   a memory capable of storing projection data;
   a rebinning circuit connected to said memory and said modification circuit; and
   said modification circuit modifying rebinned projection data.

31. A system as recited in claim 30, comprising:
   said estimation circuit producing boundary information of said high absorption object; and
   said modification circuit modifying rebinned projection data using said boundary information.

32. A system as recited in claim 26, comprising:
   a superposition circuit connected to said reconstruction circuit.

33. A system as recited in claim 32, comprising:
   said estimation circuit generating boundary information of said high absorption object;
   said superposition circuit using said boundary information to superpose high absorption object data on said radiographic image.

34. A system as recited in claim 26, wherein said estimation circuit comprises means for using a central slice theorem to estimate a boundary of said high absorption object.

35. A system as recited in claim 26, comprising:
   a Fourier analysis circuit connected to said extraction and said estimation circuits.

36. A system as recited in claim 35, comprising:
   said Fourier analysis circuit performing a Fourier transform on said radiographic image and producing a second image;
   said estimation circuit using said second image to estimate said high absorption object boundary.

37. A system as recited in claim 36, comprising:
   said modification circuit using said estimate to modify projection data corresponding to said radiographic image; and
   said reconstruction circuit reconstructing said radiographic image using modified projection data.

38. A system as recited in claim 37, comprising:
   a superposition circuit connected to said reconstruction circuit and using said boundary information to superimpose high absorption object data on said radiographic image.

39. A system as recited in claim 38, comprising:
   an output device for outputting one of said radiographic image, an image corresponding to said modified projection data, and said radiographic image having said high absorption object data superimposed thereon.

40. A system as recited in claim 26, wherein said modifying circuit is adapted to perform connectivity checking.

41. A system as recited in claim 40, wherein said modifying circuit is adapted to perform connectivity checking on at least two views of said radiographic image.

42. A system as recited in claim 26, wherein said high absorption object is a metal pin.

43. A computer program product, comprising:
   a computer storage medium and a computer program code mechanism embedded in the computer storage medium for processing an image, the computer program code mechanism comprising:
   a first computer code device configured to extract a high absorption object image from a radiographic image of a subject;
   a second computer code device configured to generate boundary information of said high absorption object; and
   a third computer code device configured to modify said radiographic image using said boundary information.

44. A computer program product as recited in claim 43, comprising:
   said second code device being configured to detect a boundary of said high absorption object.

45. A computer program product as recited in claim 44, comprising:
   said third code device being configured to modify projection data related to said radiographic image using said boundary.

46. A computer program product as recited in claim 45, comprising:
   a fourth code device being configured to reconstruct said radiographic image using modified projection data.

47. A computer program product as recited in claim 46, comprising:
   a fifth code device configured to superpose a high absorption object image on a reconstructed image.

* * * * *